United States Patent
May et al.

(10) Patent No.: US 6,228,660 B1
(45) Date of Patent: *May 8, 2001

(54) CAPILLARY IMMUNOASSAY AND DEVICE THEREFOR COMPRISING MOBILIZABLE PARTICULATE LABELLED REAGENTS

(75) Inventors: Keith May, Bedfordshire; Michael Evans Prior, Northamptonshire; Ian Richards, Bedford, all of (GB)

(73) Assignee: Conopco Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/474,192

(22) Filed: Jun. 7, 1995

Related U.S. Application Data

(62) Continuation of application No. 08/102,313, filed on Jul. 15, 1993, now Pat. No. 5,622,871, which is a continuation of application No. 07/876,449, filed on Apr. 30, 1992, now abandoned, which is a division of application No. 07/795,266, filed on Nov. 19, 1991, now abandoned, which is a continuation of application No. 07/294,146, filed as application No. PCT/GB88/00322 on Apr. 26, 1988, now abandoned.

(30) Foreign Application Priority Data

Apr. 27, 1908 (GB) .................................................... 8709873
Oct. 30, 1988 (GB) .................................................... 8725457

(51) Int. Cl.$^7$ .............................................. G01N 33/533
(52) U.S. Cl. .............................. 436/514; 422/55; 422/56; 422/57; 422/58; 435/7.92; 435/962; 435/969; 435/970; 436/518; 436/525; 436/531; 436/533; 436/534; 436/810; 436/814; 436/817; 436/818
(58) Field of Search .................................. 422/55, 56, 57, 422/58; 435/7.92, 962, 969, 970; 436/514, 518, 525, 531, 533, 534, 810, 814, 817, 818

(56) References Cited

U.S. PATENT DOCUMENTS

Re. 29,169    4/1977   Schuurs et al. .
3,410,839    11/1968   De Carvalho .
3,420,205     1/1969   Morison .

(List continued on next page.)

FOREIGN PATENT DOCUMENTS 6007486    7/1985   (AU) .
1185882   11/1981   (CA) .
1273306    8/1990   (CA) .

(List continued on next page.)

OTHER PUBLICATIONS

Carpenter et al, Elsevier Science Publishers B.V. (Biomedical Division), 1987.
Crowe et al, J. Biochem., 242:1–10 (1987).
Ikram et al, J. of Virological Methods, 13:143–148 (1986).

(List continued on next page.)

*Primary Examiner*—Long V. Le
*Assistant Examiner*—Bao-Thuy L. Nguyen
(74) *Attorney, Agent, or Firm*—Pillsbury Madison & Sutro LLP

(57) ABSTRACT

An analytical test device useful for example in pregnancy testing, comprises a hollow casing (500) constructed of moisture-impervious solid material, such as plastics materials, containing a dry porous carrier (510) which communicates indirectly with the exterior of the casing via a bibulous sample receiving member (506) which protrudes from the casing such that a liquid test sample can be applied to the receiving member and permeate therefrom to the porous carrier, the carrier containing in a first zone a labelled specific binding reagent is freely mobile within the porous carrier when in the moist state, and in a second zone spatially distinct from the first zone unlabelled specific binding reagent for the same analyte which unlabelled reagent is permanently immobilized on the carrier material and is therefore not mobile in the moist state, the two zones being arranged such that liquid sample applied to the porous carrier can permeate via the first zone into the second zone, and the device incorporating means, such as an aperture (508) in the casing, enabling the extent (if any) to which the labelled reagent becomes bound in the second zone to be observed. Preferably the device includes a removable cap for the protruding bibulous member.

14 Claims, 5 Drawing Sheets

U.S. PATENT DOCUMENTS

| | | | |
|---|---|---|---|
| 3,437,449 | 4/1969 | Luckey . | |
| 3,475,129 | 10/1969 | Peurifoy et al. . | |
| 3,620,677 | 11/1971 | Morison . | |
| 3,666,421 | 5/1972 | Price . | |
| 3,720,760 | 3/1973 | Bennich et al. | 424/1 |
| 3,723,064 | 3/1973 | Liotta . | |
| 3,744,975 | 7/1973 | Mailen . | |
| 3,798,004 | 3/1974 | Zerachia et al. . | |
| 3,811,840 | 5/1974 | Bauer | 435/810 X |
| 3,850,578 | 11/1974 | McConnell . | |
| 3,876,504 | 4/1975 | Koffler . | |
| 3,915,647 | 10/1975 | Wright . | |
| 3,981,981 | 9/1976 | Reunanen | 424/1.5 |
| 4,016,043 | 4/1977 | Schuurs et al. . | |
| 4,018,662 | 4/1977 | Ruhenstroth-Bauer et al. . | |
| 4,042,335 | 8/1977 | Clement | 422/56 |
| 4,087,326 | 5/1978 | Kereluk . | |
| 4,087,332 | 5/1978 | Hansen . | |
| 4,094,647 | 6/1978 | Deustch et al. | 435/7.9 |
| 4,116,638 | 9/1978 | Kenoff | 422/99 |
| 4,120,945 | 10/1978 | Gutcho et al. | 424/1 |
| 4,123,173 | 10/1978 | Bullock et al. | 356/246 |
| 4,133,639 | 1/1979 | Harte . | |
| 4,145,186 | 3/1979 | Andersen . | |
| 4,166,102 | 8/1979 | Johnson | 424/1 |
| 4,168,146 | 9/1979 | Grubb et al. | 435/7.9 |
| 4,169,138 | 9/1979 | Jonsson | 424/12 |
| 4,180,383 | 12/1979 | Johnson | 422/69 |
| 4,191,533 | 3/1980 | Bohn et al. . | |
| 4,219,335 | 8/1980 | Ebersole . | |
| 4,225,558 | 9/1980 | Peterson et al. | 422/72 |
| 4,230,683 | 10/1980 | Decker | 424/1 |
| 4,233,029 | 11/1980 | Columbus . | |
| 4,233,286 | 11/1980 | Soothill et al. | 424/12 |
| 4,237,234 | 12/1980 | Meunier | 435/301 |
| 4,244,916 | 1/1981 | Guigan | 422/72 |
| 4,244,940 | 1/1981 | Jeong et al. | 424/1 |
| 4,246,339 | 1/1981 | Cole et al. | 435/7 |
| 4,248,965 | 2/1981 | Mochida et al. | 435/7 |
| 4,256,724 | 3/1981 | Rutner et al. | 424/1 |
| 4,256,725 | 3/1981 | Rutner et al. | 424/1 |
| 4,258,001 | 3/1981 | Pierce et al. | 422/56 |
| 4,267,270 | 5/1981 | Stout | 435/7.9 |
| 4,270,921 | 6/1981 | Graas . | |
| 4,274,832 | 6/1981 | Wu et al. | 422/56 X |
| 4,278,651 | 7/1981 | Hales | 424/1 |
| 4,279,862 | 7/1981 | Bretaudiere et al. | 422/72 |
| 4,279,885 | 7/1981 | Reese et al. | 424/1 |
| 4,298,345 | 11/1981 | Sodickson et al. . | |
| 4,301,139 | 11/1981 | Feingers et al. | 424/1 |
| 4,302,536 | 11/1981 | Longenecker | 435/7.9 |
| 4,313,734 | 2/1982 | Leuvering | 436/525 |
| 4,315,908 | 2/1982 | Zer | 424/1 |
| 4,323,536 | 4/1982 | Columbus | 422/56 |
| 4,326,008 | 4/1982 | Rembaum | 428/403 |
| 4,332,783 | 6/1982 | Pernice et al. | 424/1 |
| 4,338,094 | 7/1982 | Elahi . | |
| 4,347,312 | 8/1982 | Brown et al. | 435/7.9 |
| 4,363,874 | 12/1982 | Greenquist | 435/7.9 |
| 4,366,241 | 12/1982 | Tom et al. | 435/7.9 |
| 4,373,812 | 2/1983 | Stein et al. | 356/246 |
| 4,373,932 | 2/1983 | Gribanau et al. | 436/501 |
| 4,374,925 | 2/1983 | Litman et al. | 435/7.9 |
| 4,380,580 | 4/1983 | Boguslaski et al. | 435/7.9 |
| 4,411,518 | 10/1983 | Meserol et al. | 356/39 |
| 4,425,438 | 1/1984 | Bauman et al. | 436/527 |
| 4,427,779 | 1/1984 | Reckel et al. | 436/507 |
| 4,435,504 | 3/1984 | Zuk | 435/7.9 |
| 4,442,204 | 4/1984 | Greenquist et al. | 435/7.9 |
| 4,444,193 | 4/1984 | Fogt et al. | 128/632 |
| 4,446,232 | 5/1984 | Liotta | 435/7.9 |
| 4,447,526 | 5/1984 | Rupchock et al. | 435/7.9 |
| 4,452,901 | 6/1984 | Gordon | 436/506 |
| 4,454,226 | 6/1984 | Ali et al. | 435/7.9 |
| 4,457,916 | 7/1984 | Hayashi et al. | 424/101 |
| 4,461,829 | 7/1984 | Greenquist | 435/7.9 |
| 4,469,787 | 9/1984 | Woods | 435/7.9 |
| 4,474,878 | 10/1984 | Halbert et al. | 435/7.9 |
| 4,483,921 | 11/1984 | Cole | 435/7.1 |
| 4,483,928 | 11/1984 | Suzuta et al. | 436/519 |
| 4,483,929 | 11/1984 | Szoka | 436/533 |
| 4,493,793 | 1/1985 | Chu | 435/7.1 |
| 4,503,143 | 3/1985 | Gerber et al. | 435/7.9 |
| 4,515,889 | 5/1985 | Klose et al. | 435/4 |
| 4,517,288 | 5/1985 | Giegel et al. | 435/7.9 |
| 4,518,565 | 5/1985 | Boger et al. | 422/58 |
| 4,526,871 | 7/1985 | Avrameas et al. | 436/504 |
| 4,552,839 | 11/1985 | Gould | 435/7.9 |
| 4,554,256 | 11/1985 | Sasser et al. | 436/510 |
| 4,568,102 | 2/1986 | Dauvergne | 280/752 |
| 4,587,102 | 5/1986 | Nagatomo et al. | 422/56 |
| 4,590,170 | 5/1986 | Akiyoshi et al. | 436/533 |
| 4,592,338 | 6/1986 | Blackmore | 128/1 R |
| 4,594,327 | 6/1986 | Zuk | 436/514 |
| 4,595,656 | 6/1986 | Allen et al. | 435/7.9 |
| 4,608,246 | 8/1986 | Bayer et al. | 424/7.9 |
| 4,650,769 | 3/1987 | Kakimi et al. | 436/533 |
| 4,656,129 | 4/1987 | Wagner | 436/501 X |
| 4,659,678 | 4/1987 | Forrest et al. | 436/512 |
| 4,666,866 | 5/1987 | Krauth | 436/518 |
| 4,668,638 | 5/1987 | Janoff et al. | 436/506 |
| 4,670,406 | 6/1987 | Allen et al. | 436/500 |
| 4,678,757 | 7/1987 | Rapkin | 436/169 |
| 4,693,970 | 9/1987 | O'Connell et al. | 435/7.9 |
| 4,695,554 | 9/1987 | O'Connell | 436/528 |
| 4,703,017 | 10/1987 | Campbell et al. | 436/501 |
| 4,713,249 | 12/1987 | Schröder | 424/488 |
| 4,740,468 | 4/1988 | Weng et al. | 435/7.92 |
| 4,742,011 | 5/1988 | Blake et al. | 436/518 |
| 4,743,560 | 5/1988 | Campbell et al. | 436/501 |
| 4,757,002 | 7/1988 | Joo | 435/7.9 |
| 4,762,857 | 8/1988 | Bollin, Jr. et al. | 514/777 |
| 4,774,192 | 9/1988 | Terminiello et al. | 436/530 |
| 4,775,515 | 10/1988 | Cottingham | 422/73 |
| 4,803,170 | 2/1989 | Stanton et al. | 436/518 |
| 4,806,311 | 2/1989 | Greenquist | 422/56 |
| 4,806,312 | 2/1989 | Greenquist | 422/56 |
| 4,810,470 | 3/1989 | Burkhardt | 422/56 |
| 4,837,145 | 6/1989 | Liotta | 435/7.9 |
| 4,837,168 | 6/1989 | de Jaenger et al. | 436/533 |
| 4,849,337 | 7/1989 | Calenoff et al. | 435/7.9 |
| 4,851,356 | 7/1989 | Canfield et al. | 436/510 |
| 4,855,240 | 8/1989 | Rosenstein et al. | 436/514 |
| 4,857,453 * | 8/1989 | Ullman et al. | 435/7.92 |
| 4,861,552 | 8/1989 | Masuda et al. | 422/56 |
| 4,861,711 | 8/1989 | Friesen et al. | 435/7.92 |
| 4,868,106 | 9/1989 | Ito et al. | 435/7.9 |
| 4,868,108 | 9/1989 | Bahar et al. | 435/7.9 |
| 4,874,710 | 10/1989 | Piran | 436/518 |
| 4,889,816 | 12/1989 | Davis et al. | 436/518 |
| 4,891,319 | 1/1990 | Roser | 435/188 |
| 4,900,663 | 2/1990 | Wie et al. | 435/7.9 |
| 4,904,583 | 2/1990 | Mapes et al. | 435/7.9 |
| 4,906,439 | 3/1990 | Grenner | 422/56 |
| 4,916,056 | 4/1990 | Brown, III et al. | 435/7.9 |
| 4,938,927 | 7/1990 | Kelton et al. | 422/64 |
| 4,956,275 * | 9/1990 | Zuk et al. | 435/7.92 |
| 4,956,302 | 9/1990 | Gordon | 436/161 |
| 4,960,691 | 10/1990 | Gordon | 435/6 |
| 4,963,468 | 10/1990 | Olson | 435/7.9 |
| 4,981,786 | 1/1991 | Dafforn et al. | 435/7.9 |

| | | | |
|---|---|---|---|
| 4,999,285 | * 3/1991 | Stiso | 435/7.9 |
| 5,026,653 | 6/1991 | Lee et al. | 436/518 |
| 5,030,558 | 7/1991 | Litman et al. | 435/7.91 |
| 5,073,340 | 12/1991 | Covington | 422/56 |
| 5,073,484 | 12/1991 | Swanson | 435/7.92 |
| 5,079,142 | * 1/1992 | Coleman et al. | 435/7.92 |
| 5,089,394 | 2/1992 | Chun | 435/34 |
| 5,120,643 | 6/1992 | Ching et al. | 435/7.92 |
| 5,141,875 | 8/1992 | Kelton et al. | 436/514 |
| 5,591,645 | * 1/1997 | Rosenstein | 436/514 |
| 5,602,040 | * 2/1997 | May et al. | 436/514 |
| 5,622,871 | * 4/1997 | May et al. | 436/514 |
| 5,656,503 | * 8/1997 | May et al. | 436/514 |

FOREIGN PATENT DOCUMENTS

| | | | |
|---|---|---|---|
| 63810 | 11/1982 | (EP) . | |
| 125118 | 11/1984 | (EP) . | |
| 97952 | 11/1984 | (EP) . | |
| 0 140 489 | 5/1985 | (EP) . | |
| 0149168 | 7/1985 | (EP) . | |
| 0212603 | 8/1985 | (EP) . | |
| 0154749 | 9/1985 | (EP) . | |
| 158746 | 10/1985 | (EP) . | |
| 0170746 | 2/1986 | (EP) . | |
| 10174247 | 3/1986 | (EP) . | |
| 30174247 | 3/1986 | (EP) . | |
| 0183442 | 6/1986 | (EP) . | |
| 0186799 | 7/1986 | (EP) . | |
| 186100 | 7/1986 | (EP) . | |
| 0191640 | 8/1986 | (EP) . | |
| 0199205 | 10/1986 | (EP) . | |
| 0212599 | 3/1987 | (EP) . | |
| 0250137 | 12/1987 | (EP) . | |
| 0 249 418 | * 12/1987 | (EP) | 436/518 |
| 253581 | 1/1988 | (EP) . | |
| 0255342 | 2/1988 | (EP) . | |
| 279097 | 8/1988 | (EP) . | |
| 0281201 | 9/1988 | (EP) . | |
| 0284232 | 9/1988 | (EP) . | |
| 0286371 | 10/1988 | (EP) . | |
| 0299428 | 1/1989 | (EP) . | |
| 0303784 | 2/1989 | (EP) . | |
| 1526708 | 9/1978 | (GB) . | |
| 2016687 | 9/1979 | (GB) . | |
| 2086041 | 5/1982 | (GB) . | |
| 2111676 | 7/1983 | (GB) . | |
| 485925 | 1/1973 | (JP) . | |
| 536465 | 2/1978 | (JP) . | |
| 59-122950 | 7/1984 | (JP) . | |
| WO8001515 | 7/1980 | (WO) . | |
| WO8102790 | 10/1981 | (WO) . | |
| WO 8603839 | 7/1986 | (WO) . | |
| WO 86/04683 | 8/1986 | (WO) . | |
| WO 87/00196 | 1/1987 | (WO) . | |
| WO 87/02774 | 5/1987 | (WO) . | |

OTHER PUBLICATIONS

Ansari et al, J. Immunological Methods, 84:117–124 (1985).

Hellman et al, Biochirmica As Biophysica Acta, 749:133–142 (1983).

Arakawa et al, Biochemistry, 21:6536–6544 (1982).

Lee et al, J. of Biological Chemistry, 256(14):7193–7201 (19981).

Carpenter et al, International Symposium on Biological Product Freeze–Drying and Formulation (1990).

Obringer et al, J. of Immunological Methods, 185:81–93 (1995).

Yoshioka et al, J. of Chromatography, 566:361–368 (1991).

Blanchard et al, J. of Immunological Methods, 130:263–275 (1990).

Miller III et al, J. of immunological Methods, 125:35–40 (1989).

Eckerskorn et al, Eur. J. Biochem, 176:509–519 (1988).

Aebersold et al, J. of Biological Chemistry, 261(9):4229–4238 (1986).

Vanderkerckhove et al, Eur. J. Biochem., 152:9–19 (1985).

Kato et al, J. Biochem, 82:261–266 (1977).

Jones, IVD Technology 32, (1999).

Miller et al, Pharmaceutical Research, 15(8):1215–1221 (1998).

Kenna, et al., "Methods for Reducing Non–Specific Antibody Binding in Enzyme–Linked Immunosorbent Assays", Journal of Immunological Methods, 85 (1985) pp. 409–419.

Vogt, Jr. et al., "Quantitative differences among various proteins as blocking agents for ELISA microtiter plates", Journal of Immunological Methods, 101 (1987) pp. 43–50.

Romano et al., "An Antiglobulin Reagent Labelled With Colloidal Gold For Use In Electron Microscopy", Immunochemistry, 1974, vol. 11, pp. 521–522.

Frens, G., Nature Physical Science, "Controlled Nucleation for the Regulation of the Particle Size in Monodisperse Gold Suspensions", vol. 241, Jan. 1, 1973, pp. 1–3.

Hoye, Age, "Determination of Radiochemical . . . High–Voltage Electrophoresis", Journal of Chromatography, 28 (1967), pp. 379–384.

Hsu, "Immunogold for Detection of Antigen on Nitrocellulose Paper", Analytical Biochemistry, vol. 142, (1984), pp. 221–225.

Surek et al., "Visualization Of Antigenic . . . Method", Biochemical and Biophysical Research Communications, vol. 121, May 1, 1984, pp. 284–289.

Geoghegan et al., "Passive Gold . . . Hemagglutination", Journal of Immunological Methods, 34, (1980), pp. 11–21.

R. Brdicka, "Grundlagen Der Physikalischen Chemie", Berlin 1958, pp. 775, 784–787, (and English translation).

Zsigmondy, "Ueber wassrige Losungen metallischen goldes", Annalen der Chemie, 301 (1898), pp. 28–55, (and English translation).

Sahlbom, Kolloidchemische Beihefte, Band II, (1910–1911), pp. 78–141, (and English translation).

Zuk, et al. "Enzyme Immunochromatography—A Quantitative Immunoassay Requiring No Instrumentation", Clinical Chemistry, vol. 31, No. 7, 1985, pp. 1144–1150.

Van Hell, et al., "Particle immunoassays", Chapter 4, Alternative Immunoassays, Collins, (1985) pp. 39–58.

Bosch, M.G., "Enzym–und Sol Particle Immunoassays for Hormone,", Archives of Gynecology and Obstetrics, vol. 242, No. 1–4, (1987), pp. 509–512 (and English translation).

Moecremans, et al., "Sensitive Visualization . . . Straining", Journal of Immunological Methods, 74 (1984) pp. 353–360.

Leuvering, et al., "Sol Particle Immunoassay (SPIA)", Abstract, Journal Of Immunoassay, 1 (1), pp. 77–91 (1980).

Leuvering et al. "Optimization of a Sandwich Sol Particle Immunoassay for Human Chorionic Gonadotrophin", Journal of Immunological Methods, Nov. 1, 1982, vol. 2, pp. 175–184.

Glad et al, Analytical Biochemistry (B5) 1978, pp. 180–187.

Gribnau et al, J. Chromatography 376 (1986) pp. 175–189.

J. Sharon et al, Detection of . . . Antibodies, Proc. Nat. Acad. Sci. USA., 76, pp 1420–1424, (1979).

G.B. Wisdom, "Enzyme–Immunoassay", Clinical Chemistry, 22, 1248–1255, 1976.

Micheel et al, "A Solid–Phase . . . Filters", Acta Histochem, vol. 71, pp 15–18 (1982).

Hawkes et al, "A Dot–Immunobinding Assay . . . Antibodies", Analytical Biochemistry, vol. 119, pp 142–147 (1982).

Esen et al, "A Simple and Rapid . . . Prolamins", Analytical Biochemistry, vol. 132, pp 462–467 (1983).

Bennett et al, "An improved Procedure . . Supernatants", Journal of Immunological Methods, vol. 61, pp 201–207 (1983).

Norgaard–Pedersen, "A Highly Sensitive . . . α–Fetoprotein", Clin. Chem. Acta, vol. 48, pp 345–346, (1973).

Langone et al, "Immunochemical Techniques", Methods In Enzymology, vol. 73, pp; 339, 340, 346–348, (1981).

Syva/a Syntex Co., AccuLevel TDM Assays, Pamphlet, pp 1–6, (1987).

T.C.J. Gribnau et al, "Affinity Chromatography . . . Techniques", Elsevier Scientific Pub. Co., pp 411–424, (1982).

Laurell et al, "Electroimmuoassay", Academic Press, vol. 73, pp 339, 340, 346–348 (1981).

* cited by examiner

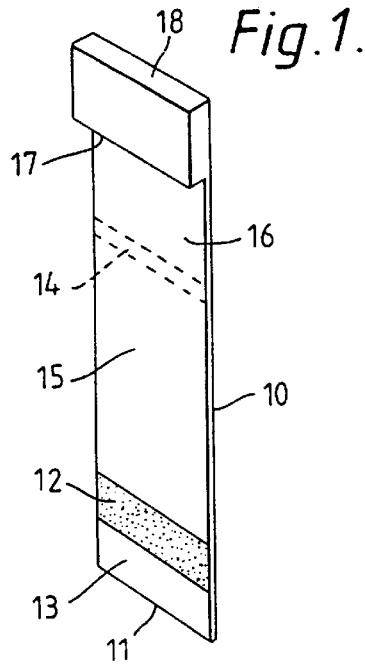
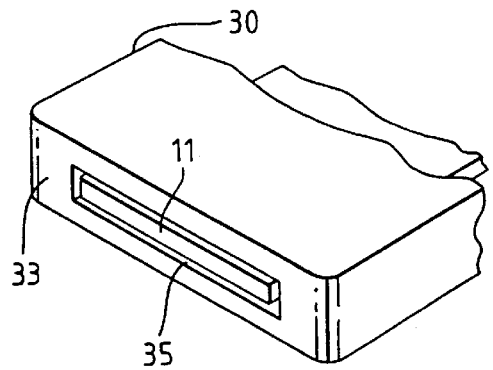
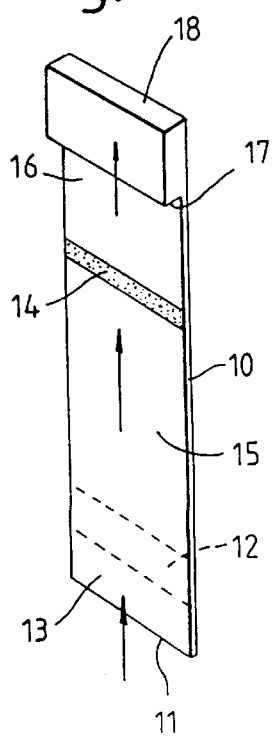
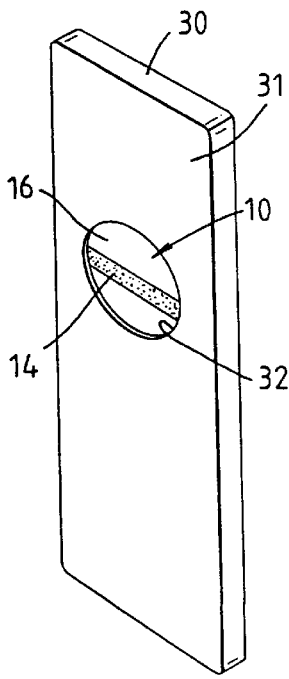
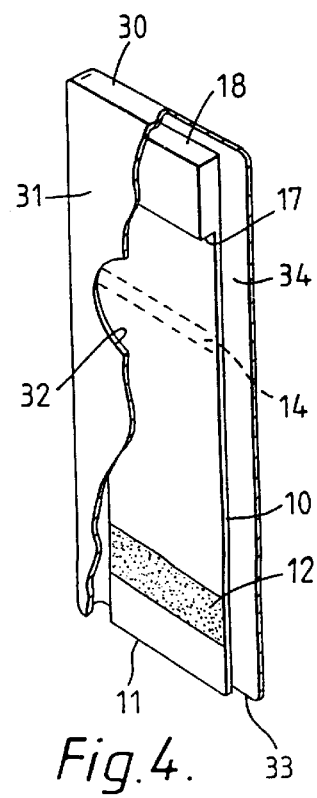

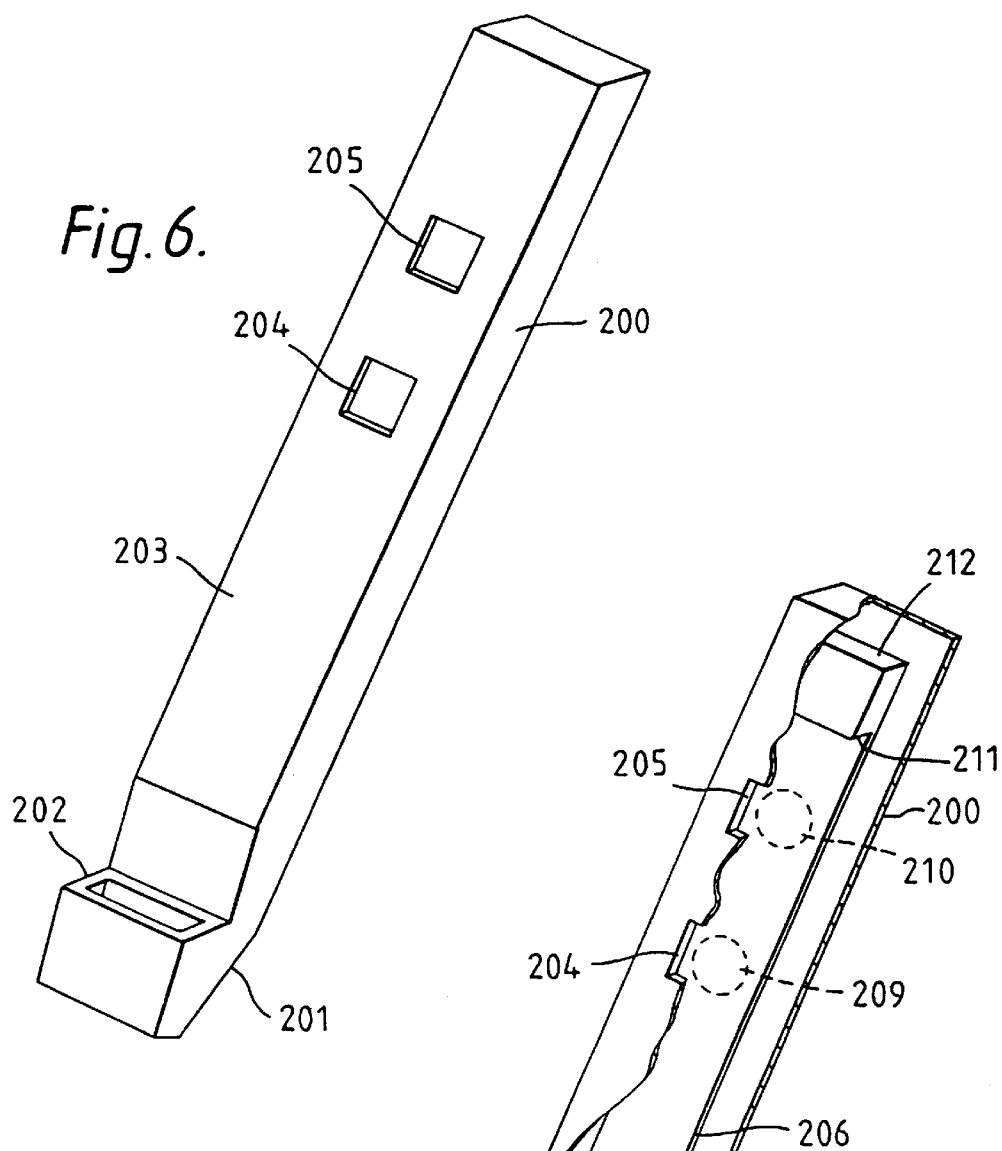

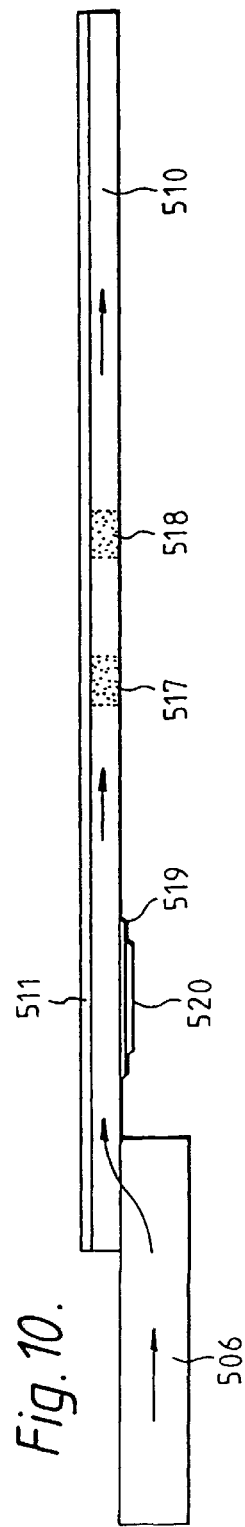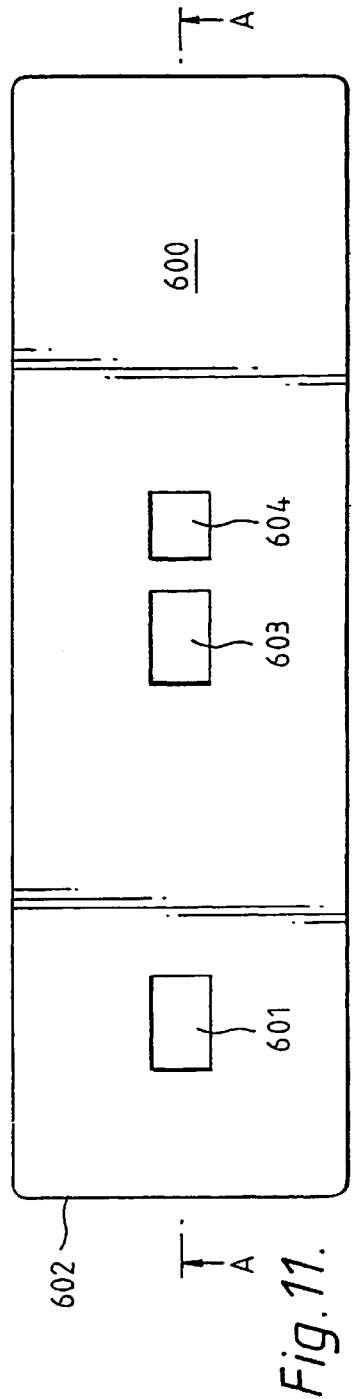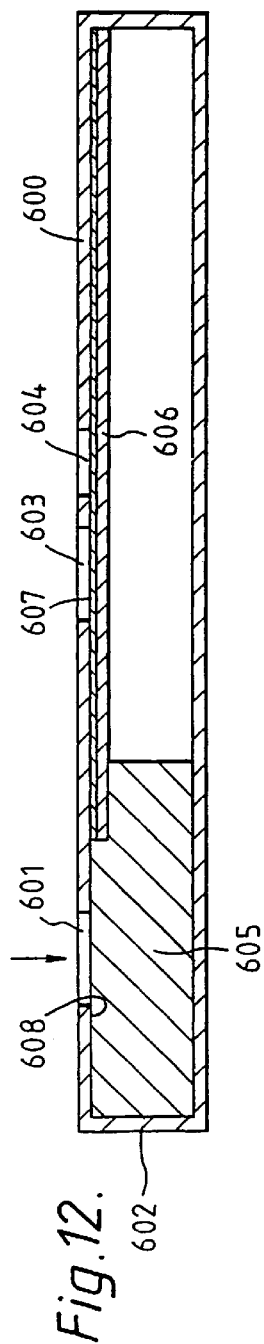

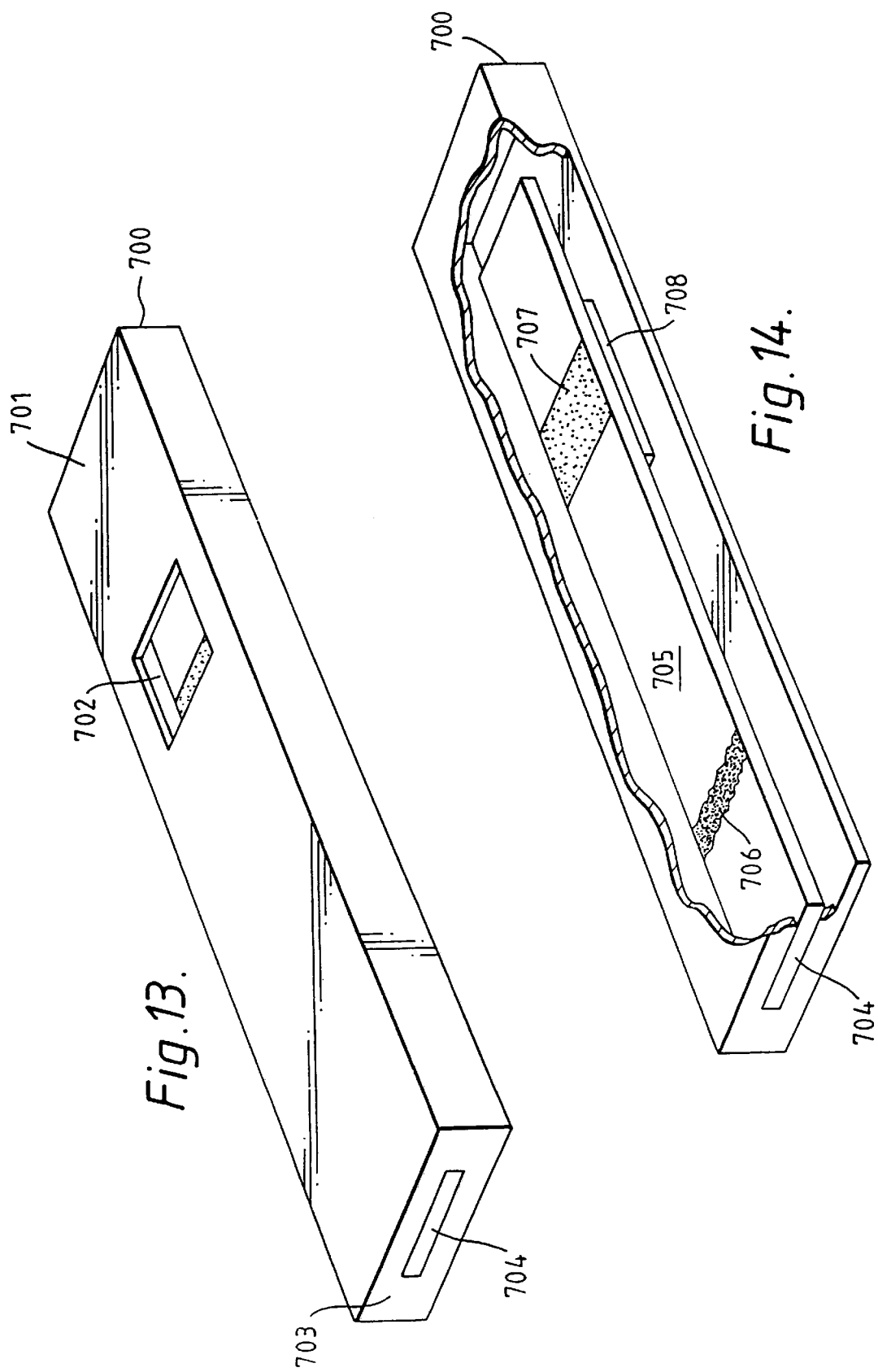

CAPILLARY IMMUNOASSAY AND DEVICE THEREFOR COMPRISING MOBILIZABLE PARTICULATE LABELLED REAGENTS

This is a continuation of application Ser. No. 08/102,313, filed Jul. 15, 1993, now U.S. Pat. No. 5,622,871, which was a continuation of 07/876,449 filled Apr. 30, 1992, now abandoned; which was a division of application Ser. No. 07/795,266, filed Nov. 19, 1991, now abandoned; which was a continuation of application Ser. No. 07/294,146, filed Feb. 27, 1989, now abandoned, which was a U.S. national phase of PCT/GB88/00322, filed Apr. 26, 1988. Priority is claimed in this case from each of the above-listed applications.

BACKGROUND OF THE INVENTION

1. Field of the Invention

The present invention relates to analytical devices which are suitable for use in the home, clinic or doctor's surgery and which are intended to given an analytical result which is rapid and which requires the minimum degree of skill and involvement from the user.

2. Description of the Related Art

The use of test devices in the home to test for pregnancy and fertile period (ovulation) is now commonplace, and a wide variety of test devices and kits are available commercially. Without exception, the commercially-available devices all require the user to perform a sequence of operations before the test result is observable. These operations necessarily involve time, and introduce the possibility of error.

SUMMARY OF THE INVENTION

It is an object of the present invention to provide a test device which is readily usable by an unskilled person and which preferably merely requires that some portion of the device is contacted with the sample (e.g. a urine stream in the case of a pregnancy or ovulation test) and thereafter no further actions are required by the user before an analytical result can be observed. Ideally the analytical result should be observable within a matter of minutes following sample application, e.g. ten minutes or less.

The use of reagent-impregnated test strips in specific binding assays, such as immunoassays, has previously been proposed. In such procedures a sample is applied to one portion of the test strip and is allowed to permeate through the strip material, usually with the aid of an eluting solvent such as water. In so doing, the sample progresses into or through a detection zone in the test strip wherein a specific binding reagent for an analyte suspected of being in the sample is immobilised. Analyte present in the sample can therefore become bound within the detection zone. The extent to which the analyte becomes bound in that zone can be determined with the aid of labelled reagents which can also be incorporated in the test strip or applied thereto subsequently. Examples of prior proposals utilising these principles are given in Thyroid Diagnostics Inc GB 1589234, Boots-Celltech Diagnostics Limited EP 0225054, Syntex (USA) Inc EP 0183442, and Behringwerke AG EP 0186799.

The present invention is concerned with adapting and improving the known techniques, such as those referred to in the above publications, to provide diagnostic test devices especially suitable for home use which are quick and convenient to use and which require the user to perform as few actions as possible.

A typical embodiment of the invention is an analytical test device comprising a hollow casing constructed of moisture-impervious solid material containing a dry porous carrier which communicates directly or indirectly with the exterior of the casing such that a liquid test sample can be applied to the porous carrier, the device also containing a labelled specific binding reagent for an analyte which labelled specific binding reagent is freely mobile within the porous carrier when in the moist state, and unlabelled specific binding reagent for the same analyte which unlabelled reagent is permanently immobilised in a detection zone on the carrier material and is therefore not mobile in the moist state, the relative positioning of the labelled reagent and detection zone being such that liquid sample applied to the device can pick up labelled reagent and thereafter permeate into the detection zone, and the device incorporating means enabling the extent (if any) to which the labelled reagent becomes in the detection zone to be observed.

Another embodiment of the invention is a device for use in an assay for an analyte, incorporating a porous solid phase material carrying in a first zone a labelled reagent which is retained in the first zone while the porous material is in the dry state but is free to migrate through the porous material when the porous material is moistened, for example by the application of an aqueous liquid sample suspected of containing the analyte, the porous material carrying in a second zone, which is spatially distinct from the first zone, an unlabelled specific binding reagent having specificity for the analyte, and which is capable of participating with the labelled reagent in either a "sandwich" or a "competition" reaction, the unlabelled specific binding reagent being firmly immobilised on the porous material such that it is not free to migrate when the porous material is in the moist state.

The invention also provides an analytical method in which a device as set forth in the proceeding paragraph is contacted with an aqueous liquid sample suspected of containing the analyte, such that the sample permeates by capillary action through the porous solid phase material via the first zone into the second zone and the labelled reagent migrates therewith from the first zone to the second zone, the presence of analyte in the sample being determined by observing the extent (if any) to which the labelled reagent becomes bound in the second zone.

In one embodiment of the invention, the labelled reagent is a specific binding partner for the analyte. The labelled reagent, the analyte (if present) and the immobilised unlabelled specific binding reagent cooperate together in a "sandwich" reaction. This results in the labelled reagent being ground in the second zone if analyte is present in the sample. The two binding reagents must have specificities for different epitopes on the analyte.

In another embodiment of the invention, the labelled reagent is either the analyte itself which has been conjugated with a label, or is an analyte analogue, ie a chemical entity having the identical specific binding characteristics as the analyte, and which similarly has been conjugated with a label. In the latter case, it is preferable that the properties of the analyte analogue which influence its solubility or dispersibility in an aqueous liquid sample and its ability to migrate through the moist porous solid phase material should be identical to those of the analyte itself, or at least very closely similar. In this second embodiment, the labelled analyte or analyte analogue will migrate through the porous solid phase material into the second zone and bind with the immobilized reagent. Any analyte present in the sample will compete with the labelled reagent in this binding reaction. Such competition will result in a reduction in the amount of labelled reagent binding in the second zone, and a consequent decrease in the intensity of the signal observed in the second zone in comparison with the signal that is observed in the absence of analyte in the sample.

An important preferred embodiment of the invention is the selection of nitrocellulose as the carrier material. This has considerable advantage over conventional strip materials, such as paper, because it has a natural ability to bind proteins without requiring prior sensitisation. Specific binding reagents, such as immunoglobulins, can be applied directly to nitrocellulose and immobilised thereon. No chemical treatment is required which might interfere with the essential specific binding activity of the reagent. Unused binding sites on the nitrocellulose can thereafter be blocked using simple materials, such as polyvinylalcohol. Moreover, nitrocellulose is readily available in a range of pore sizes and this facilitates the selection of a carrier material to suit particularly requirements such as sample flow rate.

Another important preferred embodiment of the invention is the use of so called "direct labels", attached to one of the specific binding reagents. Direct labels such as gold sols and dye sols, are already known per se. They can be used to produce an instant analytical result without the need to add further reagents in order to develop a detectable signal. They are robust and stable and can therefore be used readily in a analytical device which is stored in the dry state. Their release on contact with an aqueous sample can be modulated, for example by the use of soluble glazes.

An important aspect of the invention is the selection of technical features which enable a direct labelled specific binding reagent to be used in a carrier-based analytical device, e.g. one based on a strip format, to give a quick and clear result. Ideally, the result of the assay should be discernable by eye and to facilitate this, it is necessary for the direct label to become concentrated in the detection zone. To achieve this, the direct labelled reagent should be transportable easily and rapidly by the developing liquid. Furthermore, it is preferable that the whole of the developing sample liquid is directed through a comparatively small detection zone in order that the probability of an observable result being obtained in increased.

Another important aspect of the invention is the use of a directly labelled specific binding reagent on a carrier material comprising nitrocellulose. Preferably the nitrocellulose has a pore size of at least one micron. Preferably the nitrocellulose has a pore size not greater than about 20 microns. In a particularly preferred embodiment, the direct label is a coloured latex particle of spherical or near-spherical shape and having a maximum diameter of not greater than about 0.5 micron. An ideal size range for such particles is from about 0.05 to about 0.5 microns.

In a further embodiment of the present invention, the porous solid phase material is linked to a porous receiving member to which the liquid sample can be applied and from which the sample can permeate into the porous solid phase material. Preferably, the porous solid phase material is contained within a moisture-impermeable casing or housing and the porous receiving member, with which the porous solid phase material is linked, extends out of the housing and can act as a means for permitting a liquid sample to enter the housing and permeate the porous solid phase material. The housing should be provided with means, e.g. appropriately placed apertures, which enable the second zone of the porous solid phase material (carrying the immobilised unlabelled specific binding reagent) to be observable from outside the housing so that the result of the assay can be observed. If desired, the housing may also be provided with further means which enable a further zone of the porous solid phase material to be observed from outside the housing and which further zone incorporates control reagents which enable an indication to be given as to whether the assay procedure has been completed. Preferably the housing is provided with a removable cap or shroud which can protect the protruding porous receiving member during storage before use. If desired, the cap or shroud can be replaced over the protruding porous receiving member, after sample application, while the assay procedure is being performed. Optionally, the labelled reagent can be incorporated elsewhere within the device, e.g. in the bibulous sample collection member, but this is not preferred.

An important embodiment of the invention is a pregnancy testing device comprising a hollow elongated casing containing a dry porous nitrocellulose carrier which communicates indirectly with the exterior of the casing via a bibulous urine receiving member which protrudes from the casing and which can act as a reservoir from which urine is released into the porous carrier, the carrier containing in a first zone a highly-specific anti-hCG antibody bearing a coloured "direct" label, the labelled antibody being freely mobile within the porous carrier when in the moist state, and in a second zone spatially distinct from the first zone an highly-specific unlabelled anti-hCG antibody which is permanently immobilised on the carrier material and is therefore not mobile in the moist state, the labelled and unlabelled antibodies having specificities for different hCG epitopes, the two zones being arranged such that a urine sample applied to the porous carrier can permeate via the first zone into the second zone, and the casing being constructed of opaque or translucent material incorporating at least one aperture through which the analytical result may be observed, together with a removable and replaceable cover for the protruding bibulous urine receiving member. A fertile period prediction device, essentially as just defined except that the analyte is LH, is an important alternative.

Such devices can be provided as kits suitable for home use, comprising a plurality (e.g. two) of devices individually wrapped in moisture impervious wrapping and packaged together with appropriate instructions to the user.

The porous sample receiving member can be made from any bibulous, porous or fibrous material capable of absorbing liquid rapidly. The porosity of the material can be unidirectional (ie with pores or fibres running wholly or predominantly parallel to an axis of the member) or multi-directional (omnidirectional, so that the member has an amorphous sponge-like structure). Porous plastics material, such as polypropylene, polyethylene (preferably of very high molecular weight), polyvinylidene flouride, ethylene vinylacetate, acrylonitrile and polytetrafluoro-ethylene can be used. It can be advantageous to pre-treat the member with a surface-active agent during manufacture, as this can reduce any inherent hydrophobicity in the member and therefore enhance its ability to take up and deliver a moist sample rapidly and efficiently. Porous sample receiving members can also be made from paper or other cellulosic materials, such as nitro-cellulose. Materials that are now used in the nibs of so-called fibre tipped pens are particularly suitable and such materials can be shaped or extruded in a variety of lengths and cross-sections appropriate in the context of the invention. Preferably the material comprising the porous receiving member should be chosen such that the porous member can be saturated with aqueous liquid within a matter of seconds. Preferably the material remains robust when moist, and for this reason paper and similar materials are less preferred in any embodiment wherein the porous receiving member protrudes from a housing. The liquid must thereafter permeate freely from the porous sample receiving member into the porous solid phase material.

If present, the "control" zone can be designed merely to convey an unrelated signal to the user that the device has worked. For example, the control zone can be loaded with an antibody that will bind to the labelled antibody from the first zone, e.g. an "anti-mouse" antibody if the labelled body is one that has been derived using a murine hybridoma, to confirm that the sample has permeated the test strip. Alternatively, the control zone can contain an anhydrous reagent that, when moistened, produces a colour change or colour formation, e.g. anhydrous copper sulphate which will turn blue when moistened by an aqueous sample. As a further alternative, a control zone could contain immobilised analyte which will react with excess labelled reagent form the first zone. As the purpose of the control zone is to indicate to the user that the test has been completed, the control zone should be located downstream from the second zone in which the desired test result is recorded. A positive control indicator therefore tells the user that the sample has permeated the required distance through the test device.

The label can be an entity the presence of which can be readily detected. Preferably the label is a direct label, ie an entity which, in its natural state, is readily visible either to the naked eye, or with the aid of an optical filter and/or applied stimulation, e.g. UV light to promote fluorescence. For example, minute coloured particles, such as dye sols, metallic sols (e.g. gold), and coloured latex particles are very suitable. Of these options, coloured latex particles are most preferred. Concentration of the label into a small zone or volume should give rise to a readily detectable signal, e.g. a strongly-coloured area. This can be evaluated by eye, or by instruments if desired.

Indirect labels, such an enzymes, e.g. alkaline phosphatase and horseradish peroxidase, can be used but these usually require the addition of one or more developing reagents such as substrates before a visible signal can be detected. Hence these are less preferred. Such additional reagents can be incorporated in the porous solid phase material or in the sample receiving member, if present, such that they dissolve or disperse in the aqueous liquid sample. Alternatively, the developing reagents can be added to the sample before contact with the porous material or the porous material can be exposed to the developing reagents after the binding reaction has taken place.

Coupling of the label to the specific binding reagent can be by covalent bonding, if desired, or by hydrophobic bonding. Such techniques are commonplace in the art, and form no part of the present invention. In the preferred embodiment, where the label is a direct label such as a coloured latex particle, hydrophobic bonding is preferred.

In all embodiments of the invention, it is essential that the labelled reagent migrates with the liquid sample as this progresses to the detection zone. Preferably, the flow of sample continues beyond the detection zone and sufficient sample is applied to the porous material in order that this may occur and that any excess labelled reagent form the first zone which does not participate in any binding reaction in the second zone is flushed away from the detection zone by this continuing flow. If desired, an absorbant "sink" can be provided at the distal end of the carrier material. The absorbent sink may comprise, for example, Whatman 3 MM chromatography paper, and should provide sufficient absorptive capacity to allow any unbound conjugage to wash out of the detection zone. As an alternative to such a sink it can be sufficient to have a length of porous solid phase material which extends beyond the detection zone.

The presence or intensity of the signal from the label which becomes bound in the second zone can provide a qualitative or quantitative measurement of analyte in the sample. A plurality of detection zones arranged in series on the porous solid phase material, through which the aqueous liquid sample can pass progressively, can also be used to provide a quantitative measurement of the analyte, or can be loaded individually with different specific binding agents to provide a multi-analyte test.

The immobilised specific binding reagent in the second zone is preferably a highly specific antibody, and more preferably a monoclonal antibody. In the embodiment of the invention involving the sandwich reaction, the labelled reagent is also preferably a highly specific antibody, and more preferably a monoclonal antibody.

Preferably the carrier material is in the form of a strip or sheet to which the reagents are applied in spacially distinct zones, and the liquid sample is allowed to permeate through the sheet or strip from one side or end to another.

If desired, a device according to the invention can incorporate two or more discrete bodies of porous solid phase material, e.g. separate strips or sheets, each carrying mobile and immobilised reagents. These discrete bodies can be arranged in parallel, for example, such that a single application of liquid sample to the device initiates sample flow in the discrete bodies simultaneously. The separate analytical results that can be determined in this way can be used as control results, or if different reagents are used on the different carriers, the simultaneous determination of a plurality of analytes in a single sample can be made. Alternatively, multiple samples can be applied individually to an array of carriers and analysed simultaneously.

The material comprising the porous solid phase is preferably nitrocellulose. This has the advantage that the antibody in the second zone can be immobilised firmly without prior chemical treatment. If the porous solid phase material comprises paper, for example, the immobilisation of the antibody in the second zone needs to be performed by chemical coupling using, for example, CNBr, carbonyldiimidazole, or tresyl chloride.

Following the application of the antibody to the detection zone, the remainder of the porous solid phase material should be treated to block any remaining binding sites elsewhere. Blocking can be achieved by treatment with protein (.e.g. bovine serum albumin or milk protein), or with polyvinylalcohol or ethanolamine, or any combination of these agents, for example. The labelled reagent for the first zone can then be dispensed onto the dry carrier and will become mobile in the carrier when in the moist state. Between each of these various process steps (sensitisation, application of unlabelled reagent, blocking and application of the labelled reagent), the porous solid phase material should be dried.

To assist the free mobility of the labelled reagent when the porous carrier is moistened with the sample, it is preferable for the labelled reagent to be applied to the carrier as a surface layer, rather than being impregnated in the thickness of the carrier. This can minimise interaction between the carrier material and the labelled reagent. In a preferred embodiment of the invention, the carrier is pre-treated with a glazing material in the region to which the labelled reagent is to be applied. Glazing can be achieved, for example, by depositing an aqueous sugar or cellulose solution, e.g. of sucrose or lactose, on the carrier at the relevant portion, and drying. The labelled reagent can then be applied to the glazed portion. The remainder of the carrier material should not be glazed.

Preferably the porous solid phase material is nitrocellulose sheet having a pore size of at least about 1 micron, even more preferably of greater than about 5 microns, and yet more preferably about 8–12 microns. Very suitable nitrocellulose sheet having a nominal pore size of up to approximately 12 microns, is available commercially from Schleicher and Schuell GmbH.

Preferably, the nitrocellulose sheet is "backed", e.g. with plastics sheet, to increase its handling strenth. This can be manufactured easily by forming a thin layer of nitrocellulose on a sheet of backing material. The actual pore size of the nitrocellulose when backed in this manner will tend to be, lower than that of the corresponding unbacked material.

Alternatively, a pre-formed sheet of nitrocellulose can be tightly sandwiched between two supporting sheets of solid material, e.g. plastics sheets.

It is preferable that the flow rate of an aqueous sample through the porous solid phase material should be such that in the untreated material, aqueous liquid migrates at a rate of 1 cm in not more than 2 minutes, but slower flow rates can be used if desired.

The spatial separation between the zones, and the flow rate characteristics of the porous carrier material, can be selected to allow adequate reaction times during which the necessary specific binding can occur, and to allow the labelled reagent in the first zone to dissolve or disperse in the liquid sample and migrate through the carrier. Further control over these parameters can be achieved by the incorporation of viscosity modifiers (e.g. sugars and modified celluloses) in the sample to slow down the reagent migration.

Preferably, the immobilised reagent in the second zone is impregnated through the thickness of the carrier in the second zone (e.g. throughout the thickness of the sheet or strip if the carrier is in this form). Such impregnation can enhance the extent to which the immobilised reagent can capture any analyte present in the migrating sample.

The reagents can be applied to the carrier material in a variety of ways. Various "printing" techniques have previously been proposed for application of liquid reagents to carriers, e.g. micro-syringes, pens using metered pumps, direct printing and ink-jet printing, and any of these techniques can be used in the present context. To facilitate manufacture, the carrier (e.g. sheet) can be treated with the reagents and then subdivided into smaller portions (e.g. small narrow strips each embodying the required reagent-containing zones) to provide a plurality of identical carrier units.

BRIEF DESCRIPTION OF THE DRAWINGS

FIG. 1 a perspective view of a strip of porous solid phase material for use in an assay test in accordance with the invention;

FIG. 2 a perspective view of a strip of porous solid phase material for use in an assay test in accordance with the invention;

FIG. 3 is a perspective view of a device utilizing a porous strip of the type illustrated in FIGS. 1 and 2;

FIG. 4 is a perspective view, partially broken away, revealing a porous strip within the device of FIG. 3;

FIG. 5 is an enlarged view of one end of the device of FIG. 3;

FIG. 6 is a perspective view of another test device according to the invention;

FIG. 7 is a perspective view, similar to FIG. 6, but partially cut away to reveal the porous test strip contained within the body of the device;

FIG. 10 is an enlarged view of the porous receiving member and test strip in the device illustrated in FIGS. 8 and 9;

FIG. 11 is a plan view of another embodiment of the invention;

FIG. 12 is a schematic cross-sectional view taken along line 12—12 in FIG. 11;

FIG. 13 is a perspective view of yet another embodiment of the invention; and

FIG. 14 is a partially cut away view of the device of FIG. 13.

Figure 8:
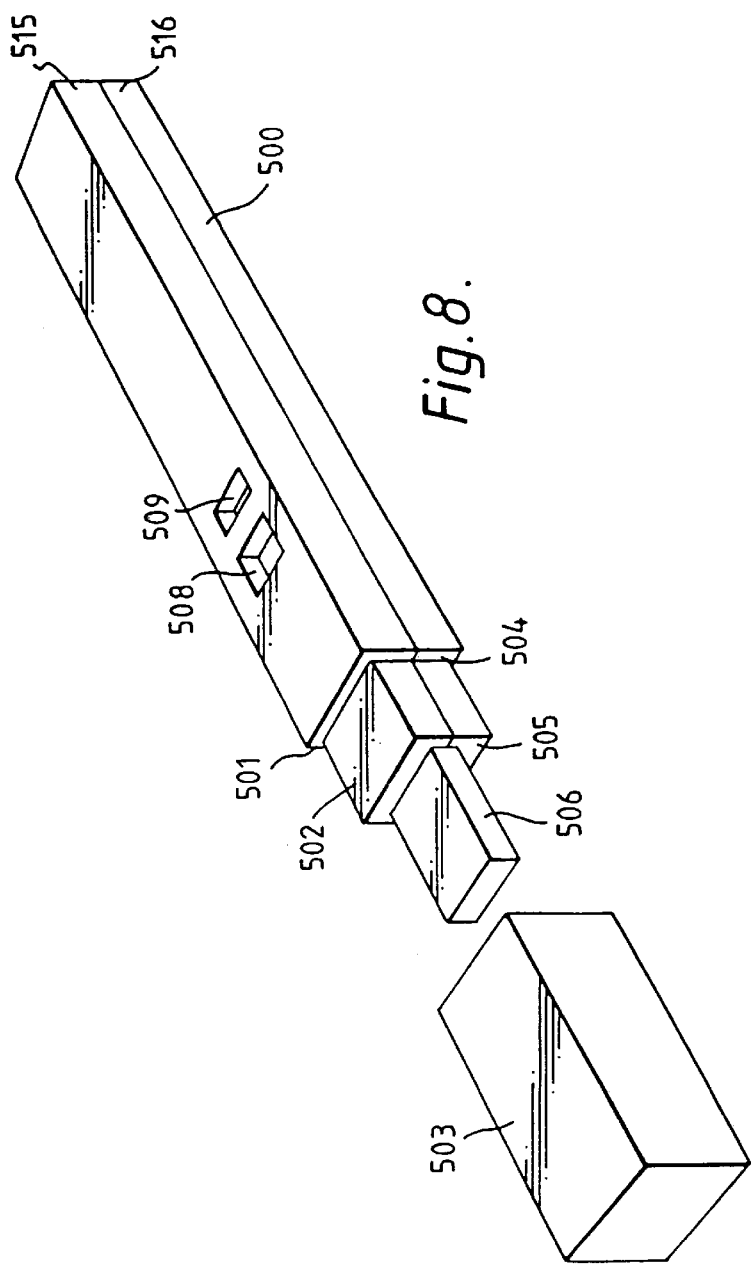
FIG. 8 is an exploded perspective view of an assay device in accordance with the present invention.

By way of example only, some preferred embodiments of the invention will now be described in detail with reference to the accompanying drawings.

EMBODIMENT 1

FIGS. 1 and 2 represent a typical strip of porous solid phase material for use in any assay test in accordance with the invention, and illustrate the underlying principle upon which the invention operates.

Referring to FIG. 1, the assay test strip 10 is seen as a rectangular strip having (for the purpose of this description) its longitudinal axis in a vertical situation. Adjacent the lower end 11 of strip 10 is a narrow band or zone 12 extending across the entire width of the strip. A small region 13 of strip 10 lies vertically below zone 12. Above zone 12 is a second zone 14 lying a discrete distance up strip 10 and similarly extending the entire width of the strip. The region 15 of strip 10 between zones 12 and 14 can be of any height as long as the two zones are separate. A further region 16 of the strip extends above zone 14, and at the top 17 of the strip is a porous pad 18 firmly linked to strip 10 such that pad 18 can act as a "sink" for any liquid sample which may be rising by capillary action through strip 10.

Zone 12 is loaded with a first antibody bearing a visible ("direct") label (e.g. coloured latex particle, dye sol or gold sol). This reagent can freely migrate through the strip in the presence of a liquid sample. In zone 14, the strip is impregnated with a second antibody having specificity for a different epitope on the same analyte as the first antibody. The second antibody is firmly immobilised on the strip.

FIG. 2 illustrates what happens when the assay strip is used in an analytical procedure. The lower end 11 of the dry strip is contacted with a liquid sample (not shown) which may contain the analyte to be determined. Capillary action causes the fluid to rise through the strip and eventually reach pad 18. In so doing, the sample traverses zone 12 and the labelled antibody will dissolve or disperse in the sample and migrate with it through the strip. While migrating towards zone 14, the labelled antibody can bind to any analyte present in the sample. On reaching zone 14, any analyte molecule should become bound to the second antibody, so immobilising the labelled "sandwhich" so produced. If a significant concentration of the analyte to be determined is present in the liquid sample, in a short period of time a distinct accumulation of the visible label should occur in zone 14.

As an example of an analysis to which this embodiment can be applied, the analyte can be hCG, the reagents in zones 12 and 14 can be monoclonal antibodies to hCG which can participate in a "sandwich" reaction with hCG, and the label can be a particulate dye, a gold sol or coloured latex particles.

Although described above in relation to a "sandwhich" reaction, it will be readily apparent to the skilled reader that this can be modified to a "competition" reaction format if desired, the labelled reagent in zone 12 being the analyte or an analogue of the analyte.

An assay based on the above principles can be used to determine a wide variety of analytes by choice of appropriate specific binding reagents. The analytes can be, for example, proteins, haptens, immunoglobulins, hormones, polynucleotides, steroids, drugs, infectious disease agents (e.g. of bacterial or viral origin) such as Streptococcus, Neisseria and Chlamydia. Sandwich assays, for example, may be performed for analytes such as hCG, LH, and infectious disease agents, whereas competition assays, for example, may be carried out for analytes such as E-3-G (estrone-3-glucuronide) and P-3-G (progesterone-3-glucuronide).

The determination of the presence (if any) of more than one analyte in sample can have significant clinical utility. For example, the ratio of the levels of apolipoproteins $A_1$ and B can be indicative of susceptibility to coronary heart disease. Similarly, the ratio of the levels of glycated haemoglobin (HbA) to unglycated (HbAo) or total (Hb) haemoglobin can aid in the management of diabetes. Additionally it is possible to configure tests to measure two steroids simultaneously, e.g E-3-G and P-3-G. By way of example, a dual analyte test for apolipoproteins $A_1$ and B may be prepared by depositing, as two spacially distinct zones, antibody specific for apolipoprotein $A_1$ throughout a first zone and depositing a second antibody specific for apolipoprotein B, throughout the second zone of a porous carrier matrix. Following the application of both antibodies to each of their respective zones via a suitable application procedure (e.g. ink-jet printing, metered pump and pen, or airbrush), the remainder of the porous material should be treated with a reagent, e.g. bovine serum albumin, polyvinyl alcohol, or ethanolamine, to block any remaining binding sites elsewhere. A third and fourth reagent, bearing a label, may then be dispensed onto the dry carrier in one or more zones near to one end of the strip, the strip being allowed to dry between applications of the two reagents to the same zone. Reagent 3 and Reagent 4 may comprise conjugates of anti-apolipoprotein $A_1$ antibody and anti-apolipoprotein B antibody respectively. Both of these conjugates will become mobile in and on the carrier when in the moist state. Reagents 3 and 4 can migrate with the solvent flow when an aqueous sample is applied to the first end of the carrier strip. While migrating towards the two zones further along the strip, reagent 3 may bind any apolipoprotein $A_1$ present in the sample and reagent 4 may bind any apolipoprotein B present in the sample. On reaching the first second-antibody zone (anti-apolipoprotein $A_1$ antibody zone) anti-apolipoprotein $A_1$ molecules should become bound to the second antibody, immobilising the labelled 'sandwich' so produced. No labelled apoliprotein B molecules will bind to this first zone. On reaching the second second-antibody zone (anti-apolipoprotein $A_1$ antibody zone) anti-apolipoprotein B molecules should become bound to the second antibody (solid-phase antibody), immobilising the labelled 'sandwich' so produced. No labelled apolipoprotein $A_1$ molecules will bind to the second zone. An accumulation of each of the direct label may occur at both or either zones to a lesser or greater extent resulting in a visible signal at either or both of the solid phase antibody zones. Excess unbound conjugate (of both reagent 3 and reagent 4) can pass freely over the two antibody zones and will be washed into the distal end of the strip.

The development of a quantifiable colour in both of the second-antibody zones may be assessed with an appropriate form of instrumentation, yielding a ratio of colour density between the two sites.

The determination of the presence of more than two (ie multiple) analytes in any example may have significant clinical utility. For example, the detection of the presence of various different serotypes of one bacterium, or the detection of the presence of soluble serological markers in humans may be useful. By way of example, a multiple analyte test for the detection of the presence of different serotypes of Streptococcus can be prepared for groups A, B, C and D. A cocktail of monoclonal antibodies, each specific for various pathologically important group serotypes, or a polyclonal antiserum raised against a particular Streptococcal group, can be dispensed onto a porous carrier strip as a line extending the width of the strip of approximately 1 mm zone length. Multiple lines be dispensed in spatially discrete zones, each zone containing immunochemically reactive component(s) capable of binding the analyte of interest. Following the application of the multiple zones, via a suitable application procedure (eg ink-jet printing, metered pump and pen, airbrush), the remainder of the porous material should be treated with a reagent (eg bovine serum albumin, polyvinylalcohol, ethanolamine) to block any remaining binding sites elsewhere. Conjugates of label, e.g. a dye sol, and each immunochemically-reactive component specific for each bacterial group may then be dispensed either onto a single zone at the bottom end of the strip, proximal to the sample application zone, or as a series of separate zones.

FIGS. 3, 4 and 5 of the accompanying drawings depict a complete device utilising a porous strip as just described above. FIG. 3 represents the complete device viewed from the front, FIG. 4 shows the same device partially cut away to reveal the details of the strip inside, and FIG. 5 shows the underside of the device.

Referring to FIG. 3, the device comprises a flat rectangular body 30 the front face 31 of which is perforated by a circular hole or window 32 which reveals the porous test strip 10 within the body. The region of the test strip 10 visible through the window 32 incorporates a narrow horizontal zone 14.

Referring to FIG. 4, the device comprises a dry rectangular test strip 10 made from porous material which extends from the bottom end 33 of the body 30 within the body between the front 31 and back 34 of the body. Near the bottom end 11 of the strip 10 is a horizontal zone 12 bearing a labelled specific binding reagent for an analyte, the binding reagent being mobile in the test strip in the moist state. Further up the test strip is the narrow horizontal zone 14 which is visible through the window 32. At the top 17 of the test strip 10 is a porous 'sink' 18 which can absorb any liquid sample that has permeated upwards through the strip.

Referring to FIG. 5, the bottom edge 35 of the body 30 incorporates a lateral aperture in which the bottom end 11 of the strip lies.

In operation, the bottom end 33 of the body 30 is immersed in a liquid sample (eg urine) so that the liquid sample can be absorbed by the bottom end 11 of the test strip 20 and rise by capillary action to the top 17 of the test strip and into the sink 18. In so doing, the liquid sample progresses via zone 12 to zone 14. Specific binding reactions as described above occur, and the test result is visible to the user through the window 32.

EMBODIMENT 2

FIGS. 6 and 7 of the accompanying drawings illustrate another test device according to the invention. FIG. 6 illustrates the complete device viewed from the front, and FIG. 7 depicts the same device partially cut away to reveal details of a porous test strip contained within the body of the device.

Referring to FIG. 6, the device comprises an elongate body 200 terminating at its lower end 201 in a small integral receptacle 202 which can hold a predetermined volume of a liquid sample, eg urine. The front face 203 of the body 200 incorporates two square small square apertures or windows 204 and 205 located one above the other.

Referring to FIG. 7, the elongate portion of the body 200 is hollow and incorporates a test strip 206 running almost the full height of the body. This test strip is of similar construction to those described under Embodiment 1, and incorporates near its lower end 207 a horizontal zone 208 bearing a labelled specific binding reagent that can freely migrate in the strip in the moist state. There are two circular zones 209 and 210 adjacent to the windows 204 and 205 and visible therethrough. The strip terminates at its top end 211 in a porous sink 212. At the bottom end 201 of the device, the receptacle 202 communicates with the hollow body via a lateral aperture 213.

In operation, a liquid sample is applied to the bottom end of the device and a predetermined volume of the sample fills the receptacle 202. From the receptacle 202 the liquid sample rises by capillary action through the test strip 206 and conveys and labelled reagent from zone 208 to the two circular zones 209 and 210. A series of specific binding reactions as described in relation to Embodiment 1 above occur. In this embodiment the second circular zone 210 can act as a control (giving rise, for example, to a coloured signal irrespective of whether or not the sample contains the analyte to be determined) and the determination of the analyte takes place in the first circular zone 209. The user can determine whether the analyte is present in the sample by comparing the signal produced in the two zones.

For example, if the test is used to determine the presence of hCG in urine during the course of a pregnancy test, the circular control zone 210 can contain immobilised HCG which will bind a labelled antibody which is carried upwards from zone 208 by the migrating liquid sample. The same labelled antibody can engage in a 'sandwich' reaction with hCG in the sample and be bound in the first circular zone 209 by another specific anti-hCG antibody which has been immobilised therein. Alternatively, if desired, the "control" zone can be designed merely to convey an unrelated signal to the user that the device has worked. For example, the second circular zone can be loaded with an antibody that will bind to the labelled antibody from zone 208, e.g. an "anti-mouse" antibody if the labelled antibody is one that has been derived using a murine hybridoma, to confirm that the sample has permeated the test strip.

EMBODIMENT 3

Figure 9:
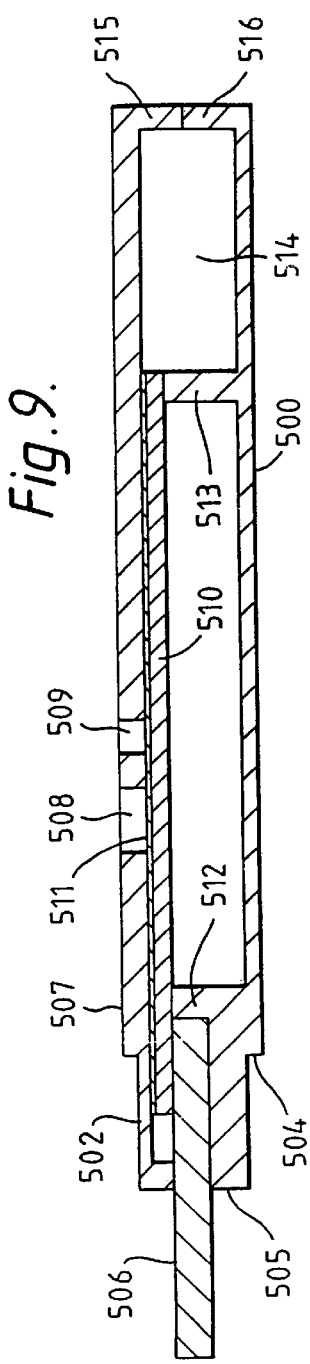
FIG. 9 is a cross-sectional side elevation of the device shown in FIG. 8.

FIG. 8 of the accompanying drawings represents an isometric view of an assay device in accordance with the invention, and FIG. 9 represents a cross-sectional side elevation of the device shown in FIG. 8.

Referring to FIG. 8, the device comprises a housing or casing 500 of elongate rectangular form having at one end 501 a portion 502 of reduced cross-sectional area. A cap 503 can be fitted onto portion 502 and can abut against the shoulder 504 at end 501 of the housing. Cap 503 is shown separated from housing 500. Extending beyond end 505 of portion 502 is a porous member 506. When cap 503 is fitted onto portion 502 of the housing, it covers porous member 506. Upper face 507 of housing 500 incorporates two apertures 508 and 509.

Referring to FIG. 9, it can be seen that housing 500 is of hollow construction. Porous member 506 extends into housing 500 and contacts a strip of porous carrier material 510. Porous member 506 and strip 510 overlap to ensure that there is adequate contact between these two materials and that a liquid sample applied to member 506 can permeate member 506 and progress into strip 510. Strip 510 extends further into housing 500. Strip 510 is "backed" by a supporting strip 511 formed of transparent moisture-impermeable plastics material. Strip 510 extends beyond apertures 508 and 509. Means are provided within housing 500 by webbs 512 and 513 to hold strip 510 firmly in place. In this respect, the internal constructional details of the housing are not a significant aspect of the invention as long as the strip is held firmly in place within the housing, and porous member 506 is firmly retained in the housing and adequate fluid permeable contact is maintained between member 506 and strip 510. The transparent backing strip 511 lies between strip 510 and apertures 508 and 509 and can act as a seal against ingress of moisture from outside the housing 500 via these apertures. If desired, the residual space 514 within the housing can contain moisture-absorbant material, such as silica gel, to help maintain the strip 510 in the dry state during storage. The reagent-containing zones in strip 510 are not depicted in FIG. 8, but the first zone containing the labelled regent which is mobile when the strip is moistened will lie in the region between the porous member 506 and aperture 508. The second zone containing the immobilised unlabelled reagent will lie in the region exposed through aperture 508 in order that when the device has been used in an assay, the result can be observed through aperture 508. Aperture 509 provides means through which a control zone containing further reagents which may enable the adequate permeation of sample through the strip to be observed.

In operation, the protective cap 503 is removed from the holder and member 506 is exposed to a liquid sample e.g. by being placed in a urine stream in the case of a pregnancy test. After exposing member 506 to the liquid sample for a time sufficient to ensure that member 506 is saturated with the sample, the cap 503 can be replaced and the device placed aside by the user for an appropriate period time (e.g. two or three minutes) while the sample permeates test strip 510 to provide the analytical result. After the appropriate time, the user can observe the test strip through apertures 508 and 509 and can ascertain whether the assay has been completed by observing the control zone through aperture 509, and can ascertain the result of the assay by observing the second zone through aperture 508.

During manufacture, the device can be readily assembled from, for example, plastics material with the housing 500 being moulded in two parts (e.g. upper and lower halves 515 and 516) which can be securely fastened together (e.g. by ultrasonic welding) after the porous member and test strip have been placed within one of the halves and then sandwiched between the two halves. The act of forming this sandwich construction can be used to "crimp" the porous member and test strip together to ensure adequate contact between them. Cap 503 can be moulded as a separate complete item. If desired, apertures 508 and 509 can be provided with transparent inserts which may insure greater security against ingress of extraneous moisture from outside the housing. By providing a tight fit between the end 505 of housing 500 and the protruding porous member 506, the application of sample to the protruding member will not result in sample entering the device directly and by-passing member 506. Member 506 therefore provides the sole route of access for the sample to the strip within the housing, and can deliver sample to the strip in a controlled manner. The device as a whole therefore combines the functions of samples and analyser.

By using the test strip materials and reagents as hereinafter described, a device in accordance with FIGS. 8 and 9 can be produced which is eminently suitable for use as a pregnancy test kit or fertile period test kit for use in the home or clinic. The user merely needs to apply a urine sample to the exposed porous member and then (after optionally replacing the cap) can observe the test result through aperture 508 within a matter of a few minutes.

Although described with particular reference to pregnancy tests and fertile period tests, it will be appreciated that the device, as just described, can be used to determine the presence of a very wide variety of analytes if appropriate reagents are incorporated in the test strip. It will be further appreciated that aperture 509 is redundant and may be omitted if the test strip does not contain any control means. Further, the general shape of the housing and cap, both in terms of their length, cross-section and other physical features, can be the subject of considerable variation without departing from the spirit of the invention.

A further option is the omission of the labelled reagent from the test strip, this reagent being added to the sample prior to application of the sample to the test device. Alternatively, the labelled reagent can be contained in the protruding porous member 506.

FIG. 10 of the accompanying drawings shows an enlarged view of the porous receiving member and test strip in the device illustrated in FIGS. 8 and 9.

The porous receiving member 506 is linked to the porous test strip 510, backed by the transparent plastics sheet 511, such that liquid can flow in the direction shown by the arrows through the porous receiving member and into the porous strip. Test zone 517 incorporates the immobilised specific binding reagent, and control zone 518 contains a reagent to indicate that the sample has permeated a sufficient distance along the test strip. A portion of the test strip surface opposite the backing strip 511 and adjacent the porous receiving member 506, carries a glaze 519 on which is deposited a layer 520 of labelled specific binding reagent. The thickness of these two layers as depicted in FIG. 10 is grossly exaggerated purely for the purpose of illustration. It will be appreciated that, in practice, the glaze may not form a true surface layer and the glazing material will penetrate the thickness of the strip to some extent. Similarly, the subsequently applied labelled reagent may also penetrate the strip. Nevertheless, the essential objective of reducing any interaction between the labelled reagent and the carrier material forming the strip will be achieved. An aqueous sample deposited in receiving member 506 can flow therefrom along the length of strip 510 and in so doing, will dissolve glaze 519 and mobilise the labelled reagent, and carry the labelled reagent along the strip and through zone 517.

Embodiment 4

FIGS. 11 and 12 illustrate another embodiment of the invention, which is seen in plan view in FIG. 11 and in cross-section in FIG. 12, the cross-section being an elevation on the line 12—12 seen in FIG. 11.

Referring to FIG. 11, the test device comprises a flat rectangular casing 600 incorporating a centrally disposed rectangular aperture 601, adjacent the left hand end 602, and two further apertures 603 and 604 near the mid point of the device and arranged such that apertures 601, 603 and 604 lie on the central longitudinal axis of the device corresponding to line 12—12. Although all three apertures are illustrated as being rectangular, their actual shape is not critical.

Referring to the cross-section seen in FIG. 12, the device is hollow and incorporates within it a porous sample receiving member adjacent end 602 of casing 600 and lying directly beneath aperture 601. A test strip of similar construction to that described with reference to Embodiment 4, comprising a porous strip 606 backed by a transparent plastics sheet 607 is also contained within casing 600, and extends from the porous receiving member 602, with which the porous carrier is in liquid permeable contact, to the extreme other end of the casing. The transparent backing sheet 607 is in firm contact with the upper inner surface 608 of casing 600, and provides a seal against apertures 603 and 604 to prevent ingress of moisture or sample into the casing. Although not shown in the drawings, the porous test strip 606 will incorporate a labelled specific binding reagent, and a test zone and a control zone placed appropriately in relation to apertures 603 and 604, in a manner analagous to that described in Embodiment 3.

In operation, an aqueous sample can be applied through aperture 601, e.g. by means of a syringe, to saturate porous receiving member 605. Thereafter, the aqueous sample can permeate the test strip and after an appropriate time the test result can be observed through apertures 603 and 604.

Embodiment 5

A yet further embodiment of the invention is illustrated in FIGS. 13 and 14 of the accompanying drawings. FIG. 13 shows a device comprising a rectangular casing 700 having in its upper surface 701 a rectangular aperture 702. One end wall 703 of the device 703 incorporates an aperture 704 through which a porous test element communicates with the exterior of the device. Aperture 702 is situated in surface 701 at a point relatively remote from the end 703 containing the aperture 704.

FIG. 14 shows a partially cut-away view of the device in FIG. 13. The hollow device incorporates a porous test strip 705, running almost the entire length of casing 700 from aperture 704. Test strip 705 incorporates a first zone 706 containing a labelled specific binding reagent and a further zone 707, remote from aperture 704, incorporating an immobilised specific reagent. Zone 706 lies directly beneath aperture 702 is therefore observable from outside casing. Beneath strip 705 and adjacent zone 707, is a crushable element 708 containing one or more substrates or reagents which can be used to produce a detectable signal when released into zone 707, if labelled reagent from 706 has become bound in zone 707 following use of the device. Release of the reagents from member 708 can be effected by applying pressure to the outside of the casing at that point in order to crush the member and express the reagent therefrom.

In operation, the first test element can be exposed to an aqueous sample, e.g. by dipping end 703 of casing 700 into a vessel containing the sample. The liquid sample will then permeate the length of test strip 705, taking labelled reagent from zone 706 and passing through zone 707 where the labelled reagent can become bound e.g. through a "sandwich" reaction involving an analyte in the sample. When the sample has permeated the test strip, reagent can be released from the crushable member 708 and the result of the test observed through aperture 702.

By way of example only, certain preferred test strip materials, reagents, and methods for their production will now be described.

1. Selection of Liquid Conductive Material

Representative examples of liquid conductive materials include paper, nitrocellulose and nylon membranes. Essential features of the material are its ability to bind protein; speed of liquid conduction; and, if necessary after pre-treatment, its ability to allow the passage of labelled antibodies along the strip. It this is a direct label, it may be desirable for the material to allow flow of particles of size up to a few microns (usually less than $0.5\mu$). Examples of flow rates obtained with various materials are given below:

|  | Pore size | Time to Flow 45 mm (minutes) |
| --- | --- | --- |
| Schleicher + Schuell nitrocellulose | $3\mu$ | 3.40 |
| (unbacked) | $5\mu$ | 3.30 |
|  | $8\mu$ | 3.00 |
|  | $12\mu$ | 2.20 |
| polyester-backed | $8\mu$ (nominal) | 3.40 |
| Whatman Nitrocellulose | 5 | 19.20 |
| Pall "Immunodyne" (nylon) | 3 | 4.00 |
|  | 5 | 3.20 |

The speed of a test procedure will be determined by the flow rate of the material employed and while any of the above materials can be used some will give faster tests than others.

Nitrocellulose had the advantage of requiring no activation and will immobilise proteins strongly by absorbtion. "Immunodyne" is pre-activated and requires no chemical treatment. Papers, such as Whatman 3MM, require chemical activation with for example carbonyldiimidazole in order to successfully immobilise antibody.

2. Labels

Preparation of Labels

A selection of labels which may be used are described below. This list is not exhaustive.

A) Gold Sol Preparation

Gold sols may be prepared for use in immunoassay from commercially-available colloidal gold, and an antibody preparation such as anti-alpha human chorionic gonadotrophin. Metallic sol labels are described, for example, in European patent specification No. EP 7654.

For example, colloidal gold G20 (20 nm particle size, supplied by Janssen Life Sciences Products) is adjusted to pH 7 with $0.22\mu$ filtered $0.1M$ $K_2CO_3$, and 20 mls is added to a clean glass beaker. 200 µl of anti-alpha hCG antibody, prepared in 2 mM borax buffer pH9 at 1 mg/ml, and $0.22\mu$ filtered, is added to the gold sol, and the mixture stirred continuously for two minutes. $0.1M$ $K_2CO_3$ is used to adjust the pH of the antibody gold sol mixture to 9, and 2 mls of 10% (w/v) BSA is added.

The antibody-gold is purified in a series of three centrifugation steps at 12000 g, 30 minutes, and 4° C., with only the loose part of the pellet being resuspended for further use. The final pellet is resuspended in 1% (w/v) BSA in 20 mM Tris, 150 mM NaCl pH 8.2.

B) Dye Sol Preparation

Dye sols (see, for example, European patent specification No. EP 32270) may be prepared from commercially-available hydrophobic dyestuffs such as Foron Blue SRP (Sandoz) and Resolin Blue BBLS (Bayer). For example, fifty grammes of dye is dispersed in 1 liter of distilled water by mixing on a magnetic stirrer for 2–3 minutes. Fractionation of the dye dispersion can be performed by an initial centrifugation step at 1500 g for 10 minutes at room temperature to remove larger sol particles as a solid pellet, with the supernatant suspension being retained for further centrifugation.

The suspension is centrifuged at 3000 g for 10 minutes at room temperature, the supernatant being discarded and the pellet resuspended in 500 mls distilled water. This procedure is repeated a further three times, with the final pellet being resuspended in 100 mls distilled water.

The spectra of dye sols prepared as described above can be measured, giving lambda-max values of approximately 657 nm for Foron Blue, and 690 nm for Resolin Blue. The absorbance at lambda-max, for 1 cm path length, is used as an arbitrary measure of the dye sol concentration.

C) Coloured Particles

Latex (polymer) particles for use in immunoassays are available commercially. These can be based on a range of synthetic polymers, such as polystyrene, polyvinyltoluene, polystyrene-acrylic acid and polyacrolein. The monomers used are normally water-insoluble, and are emulsified in aqueous surfactant so that monomer mycelles are formed, which are then induced to polymerise by the addition of initiator to the emulsion. Substantially sperical polymer particles are produced.

Coloured latex particles can be produced either by incorporating a suitable dye, such as anthraquinone, in the emulsion before polymerisation, or by colouring the preformed particles. In the latter route, the dye should be dissolved in a water-immiscible solvent, such a chloroform which is then added to an aqueous suspension of the latex particles. The particles take up the non-aqueous solvent and the dye, and can then be dried.

Preferably such latex particles have a maximum dimension of less than about 0.5 micron.

Coloured latex particles may be sensitised with protein, and in particular antibody, to provide reagents for use in immunoassays. For example, polystyrene beads of about 0.3 micron diameter, (supplied by Polymer Laboratories) may be sensitised with anti-alpha human chorionic gonadotrophin, in the process described below:

0.5 ml (12.5 mg solids) of suspension is diluted with 1 ml of 0.1M borate buffer pH 8.5 in an Eppendorf vial. These particles are washed four times in borate buffer, each wash consisting of centrifugation for 3 minutes at 13000 rpm in an MSE microcentrifuge at room temperature. The final pellet is resuspended in 1 ml borate buffer, mixed with 300 µg of anti-alpha hCG antibody, and the suspension is rotated end-over-end for 16–20 hours at room temperature. The antibody-latex suspension is centrifuged for 5 minutes at 13000 rpm, the supernatant is discarded and the pellet resuspended in 1.5 mls borate buffer containing 0.5 milligrammes bovine serum albumin. Following rotation end-over-end for 30 minutes at room temperature, the suspension is washed three times in 5 mg/ml BSA in phosphate buffered saline pH7.2, by centrifugation at 13000 rpm for 5 minutes. The pellet is resuspended in 5 mg/ml BSA/5% (w/v) glycerol in phosphate buffered saline pH 7.2 and stored at 4° C. until used.

(A) Anti-hCG—Dye Sol Preparation

Protein may be coupled to dye sol in a process involving passive adsorption. The protein may, for example, be an antibody preparation such as anti-alpha human chorionic gonadotrophin prepared in phosphate buffered saline pH 7.4 at 2 milligram/ml. A reaction mixture is prepared which contains 100 µl antibody solution, 2 mls dye sol, 2 mls 0.1M phosphate buffer pH 5.8 and 15.9 mls distilled water. After gentle mixing of this solution, the preparation is left for fifteen minutes at room temperature. Excess binding sites may be blocked by the addition of, for example, bovine serum albumin: 4 mls of 150 mg/ml BSA in 5 mM NaCl pH 7.4 is added to the reaction mixture, and after 15 minutes incubation at room temperature, the solution is centrifuged at 3000 g for 10 minutes, and the pellet resuspended in 10 mls of 0.25% (w/v) dextran/0.5% (w/v) lactose in 0.04M phosphate buffer. This antibody-dye sol conjugate is best stored in a freeze dried form.

(B) LH—Dye Sol Preparation

Due to the structural homology between the alpha subunits of hCG and LH, alpha hCG antibody can be used to detect LH in a cross-reactive immunoassay. Thus, a labelled antibody may be prepared for use in an LH assay in an identical manner to that described in Example 1, using anti-alpha hCG antibody.

3. Preparation of Reagent Strip

Zonal Impregnation of Liquid-conductive Materials

Liquid-conducting material with a restricted zone of immobilised protein, particularly antibody, can be prepared for example as follows:

A rectangular sheet of Schleicher and Schuell backed 8µ nitrocellulose measuring 25 cm in length and 20 cm in width may have a reaction zone formed upon it by applying a line of material about 1 mm wide at 5 cm intervals along its length and extending throughout its 20 cm width. The material can, for example, be a suitably selected antibody preparation such as anti-beta (human chorionic gonadotropin) of affinity Ka at $10^9$, prepared in phosphate buffered saline pH 7.4 at 2 milligram/ml, suitable for immunoassay of human chorionic gonadotrophin using a second (labelled) anti-hCG antibody in a sandwich format. This solution can be deposited by means of a microprocessor-controlled microsyringe, which delivers precise volumes of reagent through a nozzle, preferably 2 mm diameter. When the applied material has been allowed to dry for 1 hour at room temperature, excess binding sites on the nitrocellulose are blocked with an inert compound such as polyvinyl alcohol (1% w/v in 20 mM Tris pH 7.4) for 30 minutes at room temperature, and sheets are thoroughly rinsed with distilled water prior to drying for 30 minutes at 30° C.

In one embodiment, the liquid conductive material can then be cut up into numerous strips 5 cm in length and 1 cm in width, each strip carrying a limited zone of the immobilised antibody to function as an immunosorbent part way (e.g. about half way) along its length. In this example the test strip is used with a liquid label which is mixed with sample. In use, this limited zone then becomes a test reaction zone in which the immunoassay reactions take place.

In another embodiment, the label may be dispensed/deposited into/on a restricted zone before cutting up the liquid-conductive material into strips. By way of example, this reagent may be dye sol or dye polymer-conjugated anti-hCG antibody prepared as described under dye sol preparation, said reagent being retained in the zone when the material is in the dry state but which is free to migrate through the carrier material when the material is moistened, for example, by the application of liquid sample containing the analyte to be determined. This mobile reagent zone is applied, for example, as follows:

A sheet of Schleicher and Schuell backed 8µ nitrocellulose, 25 cm in length and 20 cm in width with zones of immobilised antibody at 5 cm intervals along its length, is prepared as described previously. Prior to the deposition of dye labelled antibody, a sublayer of, for example, 60% w/v of sucrose in distilled water is applied by airbrush on the microprocessor controlled system at 6 cm intervals along the length of the sheet. Then several passes (e.g. three) of dye labelled antibody prepared in 1% methacel KAM (Trademark for methylcellulose from Dow Chemical Company) and 0.6% (w/v) polyvinylalcohol are applied by airbrush or by microsyringe directly on top of the sublayer. Sheets are then allowed to dry, and cut into strips 5 cm in length and 1 cm in width, to be used in the completed device.

Gold sols, or coloured polystyrene particles can be deposited by a similar process.

In addition to the test zone various control zone options can be operated. For example a zone of anti-species IgG may be deposited after the test zone.

4. Sandwich Assays using Strip Format

A sandwich-type reaction may be performed for the detection of human chorionic gonadotrophin (hCG) in a liquid sample. Preferably the label used as a direct label which is readily visible to the naked eye. Dye sols, gold sols or coloured latex particles may be linked to anti hCG antibody, as described above.

With direct labels, assays may be performed in which fresh urine samples are applied directly from the urine stream, or by delivering an appropriate volume (e.g. 100 µl) from a container using a pipette to the absorbent wick of the test device. Each sample is allowed to run for five minutes in the device, and the colour generated at the reactive zone read either by eye, or using a light reflectometer.

Indirect labels such as enzymes e.g. alkaline phosphatase may also be used, but require the addition of substrate to generate a coloured endpoint.

Enzyme assays may be performed in which the anti-hCG antibody is conjugated to alkaline phosphatase, using conventional techniques, and diluted 1/100 in 0.01M phosphate buffered saline pH 7 containing 3% polyethylene glycol 6000, 1% (w/v) bovine serum albumin and 0.02% TRITON X305 (Trademark—obtainable from Rohm and Haas) before application to the sheet. Fresh urine samples are then applied, either directly from the urine stream, or by delivering an appropriate volume (e.g. 100 µl) from a container using a pipette, to the absorbent wick of the test device. Each sample is allowed to run for five minutes before a pad of liquid-swellable material soaked in BCIP substrate (at 1 mg/ml in 1M Tris/HCl pH 9.8) is placed in contact with the immobile antibody zone. After a further five minutes, the pad is removed, and colour generated read either by eye, or by using a light reflectometer.

A similar embodiment can be prepared using lutenising hormone (LH) instead of hCG.

5. Competitive Assays

A competitive type assay may be performed as exemplified by estrone-3-glucuronide, a urinary metabolite of estrone. Conjugates of estrone-3-glucuronide and bovine serum albumin are prepared as follows:

Preparation of BSA—Estrone-3-glucuronide

The conjugation of E-3-G and BSA may be achieved through the use of a mixed anhydride. All of the glassware, solvents and reagents employed in the preparation of the activated species must be thoroughly dried using an oven, dessicator or molecular sieves, as appropriate, for at least 24 hours.

Solutions of E-3-G (2 nM) in dry dimethylformamide (DMF) and tri-n-butylamine (TnB) (10 nM) in dry DMF were equilibrated separately at 4° C. Using pre-cooled glassware E-3-G in DMF (1.25 ml) and TnB in DMF (0.25 ml) were added to a pre-cooled 5 ml Reactivial containing a magnetic stirrer. A solution of isobutyl chloroformate in dry DMF (10 nM) was prepared and an aliquot (0.25 ml) was cooled to 4° C. and added to the Reactivial. The contents of the Reactivial were stirred for 20 minutes at 4° C. and a solution of BSA (1 mg/ml) in bicarbonate buffer (0.5%) was prepared. When the mixed anhydride incubation was complete, the contents of the Reactivial were added to the BSA solution (2.5 ml) and stirred on a magnetic stirrer for 4 hours at 4° C. The conjugate preparation was purified by passage through a Tris buffer equilibrated Pharmacia PD-10 SEPHADEX G-25 column, transferred to an amber glass storage bottle and stored at 4° C.

Preparation of BSA-E-3-G Dye Sol

A dispersion of dye (5% w/v) in distilled water was prepared with thorough mixing and aliquots were centrifuged at 3850 rpm (1500 g) for 10 minutes in a bench top centrifuge. The pellet was discarded and the supernatant was retained and centrifuged in aliquots at 4850 rpm (3000 g) for 10 minutes in a bench top centrifuge. The supernatant was discarded and the pellet was resuspended in half of its original volume in distilled water. This step was repeated four times to wash the pellet. The pellet was finally resuspended in distilled water and the absorbance at lambda max was determined.

Solutions of dye sol in distilled water and E-3-G/BSA conjugate diluted in phosphate buffer were mixed to give final concentrations of 10 µg/ml conjugate (based on BSA content) and an extrapolated dye sol optical density of 20 at the absorbance maximum. The reaction mixture was incubated for 15 minutes at room temperature and blocked for 15 minutes at room temperature with BSA in a NaCl solution (5 mM, pH 7.4) to yield a final BSA concentration of 25 mg/ml. The reaction mixture was centrifuged at 4850 rpm (3000 g) for 10 minutes in a benchtop centrifuge, the supernatant was discarded and the pellet was resuspended in half of its original volume in Dextran (0.25% w/v)/Lactose (0.5% w/v) phosphate (0.04M pH 5.8) buffer.

Preparation of E-3-G Test Strips

Antibodies to E-3-G were deposited as described in example 3. BSA—E-3G dye sol was deposited on the strips as described in 3.

Determination of E-3-G

Using reagents described above, a standard curve can be generated by running strips with samples with known concentrations of E-3-G. The colour at the immobile zone can be read, for example using a Minolta chromameter, and the concentration of E-3-G calculated by extrapolating from the reflectance value.

The invention described herein extends to all such modifications and variations as will be apparent to the reader skilled in the art, and also extends to all combinations and subcombinations of the features of this description and the accompanying drawings.

What is claimed is:

1. An analytical test device for detecting an analyte suspected of being present in a liquid biological sample and requiring solely the application thereto of said liquid biological sample to enable a test to be performed and a test result to be provided, said device comprising:

a hollow casing constructed of moisture impervious solid material;

a test strip, comprising a dry porous carrier disposed in said casing, said dry porous carrier comprising a test result zone and a control zone; and a labeled reagent capable of specifically binding with said analyte to form a first complex of said labeled reagent and said analyte, said labeled reagent being positioned within said casing as part of said dry porous carrier prior to use, said labeled reagent being a particulate direct label, said casing comprising a sample application aperture through which liquid biological sample can be applied directly or indirectly to said carrier, said labeled reagent being located upstream from said test result zone prior to use and released into mobile form by application of said liquid biological sample, wherein said carrier comprises, immobilized in said test result zone, means for binding said first complex, and wherein migration of said applied liquid biological sample through said dry porous carrier conveys by capillarity said first complex to said test result zone of said dry porous carrier, whereat said binding means binds said first complex thereby to form a second complex and to thereby indicate the presence of said analyte in said liquid biological sample, said casing further comprising a test result observation aperture remote from said sample application aperture, said test result zone at least being visible through said test result observation aperture, said sample application aperture and said test result observation aperture being spaced apart and disposed so that sample liquid can be applied to said sample application aperture to initiate said test but said test strip is substantially shielded from accidental initial application of sample liquid directly to a portion of said test strip downstream from said location of said labeled reagent in the dry state, wherein said control zone comprises a material for indicating that said liquid biological sample has been conveyed thereto by capillarity along said carrier irrespective of a presence or absence of said analyte in said liquid biological sample.

2. The analytical test device of claim 1, further comprising a control zone observation aperture, said control zone being visible through said control zone observation aperture; said control zone observation aperture being defined separately from said test result observation aperture.

3. The analytical test device of claim 1, wherein said control zone comprises means for binding labeled reagent conveyed thereto by said liquid biological sample, irrespective of a presence or absence of said analyte.

4. The analytical test device of claim 1, wherein said carrier communicates indirectly with an exterior of the casing via a sample receiving member.

5. The analytical test device of claim 4, wherein the sample receiving member protrudes through the sample application aperture.

6. The analytical test device of claim 1, wherein said casing has first and second longitudinal ends, said sample application aperture being disposed adjacent said first longitudinal end and further comprising a displaceable shroud disposed on said first end for shielding said liquid biological sample application aperture.

7. The analytical test device of claim 1, wherein said analyte is human chorionic gonadotrophin (hCG).

8. The analytical test device of claim 1, wherein said analyte is luteinizing hormone (LH).

9. The analytical test device of claim 1 wherein said label is a gold sol.

10. The analytical test device of claim 1, wherein said label is colored latex particles.

11. A pregnancy testing device for detecting human chorionic gonadotrophin (hCG) suspected of being present in a urine sample and requiring solely the application thereto of said urine sample to enable a test to be performed and a test result to be provided, said device comprising:

a hollow casing constructed of moisture impervious solid material;

a test strip, comprising a dry porous carrier disposed in said casing, said dry porous carrier having a detection zone and a control zone; and labeled reagent comprising an anti-hCG antibody bearing a particulate direct label capable of specifically binding with said hCG to form a first complex of said labeled anti-hCG antibody and said hCG, said labeled hCG antibody reagent being at least one of disposed on and contained in said test strip in a dry state prior to use, said casing comprising a sample application aperture through which urine can be applied directly or indirectly to said carrier, said labeled hCG antibody being located upstream from said detection zone prior to use and released into mobile form by application of said urine sample, wherein said carrier comprises, immobilized in said detection zone, means for binding said first complex, and wherein migration of said applied urine sample through said dry porous carrier conveys by capillarity said labeled hCG antibody and said hCG to said detection zone of said dry porous carrier, whereat said binding means binds said first complex thereby to form a second complex, thereby to indicate the presence of said hCG in said urine sample, said casing comprising a test result observation aperture remote from said sample application aperture, said detection zone at least being visible through said test result observation aperture, said sample application aperture and said test result observation aperture being spaced apart and disposed so that urine can be applied to said sample application aperture to initiate said test but said test strip is substantially shielded from accidental initial application of urine directly to a portion of said test strip downstream from said location of said labeled hCG antibody in the dry state, wherein said control zone comprises a material for indicating that said urine sample has been conveyed thereto by capillarity along said carrier irrespective of a presence or absence of hCG in said urine sample.

12. The pregnancy testing device of claim 11, wherein said control zone is downstream from said detection zone.

13. The pregnancy testing device of claim 11 wherein said label is a gold sol.

14. The pregnancy testing device of claim 11 wherein said label is colored latex particles.

* * * * *

UNITED STATES PATENT AND TRADEMARK OFFICE
CERTIFICATE OF CORRECTION

PATENT NO.    : 6,228,660 B1                                        Page 1 of 1
DATED         : May 8, 2001
INVENTOR(S)   : May et al.

It is certified that error appears in the above-identified patent and that said Letters Patent is hereby corrected as shown below:

<u>Title page,</u>
Item [30], first line of Foreign Application Priority Data should read as follows:

-- Apr. 27, 1987      (GB) ........................... 8709873 --

Signed and Sealed this

Fourteenth Day of January, 2003

JAMES E. ROGAN
*Director of the United States Patent and Trademark Office*